United States Patent [19]

Chandraratna

[11] Patent Number: 5,434,173
[45] Date of Patent: Jul. 18, 1995

[54] HETEROARYL SUBSTITUTED PHENYLETHENYL COMPOUNDS HAVING RETINOID-LIKE BIOLOGICAL ACTIVITY

[75] Inventor: Roshantha A. S. Chandraratna, El Toro, Calif.

[73] Assignee: Allergan, Inc., Irvine, Calif.

[21] Appl. No.: 126,951

[22] Filed: Sep. 24, 1993

Related U.S. Application Data

[62] Division of Ser. No. 833,682, Feb. 11, 1992, abandoned.

[51] Int. Cl.$^6$ .................. A61K 31/445; C07D 213/46
[52] U.S. Cl. .................... 514/354; 514/357; 546/314; 546/323; 546/326
[58] Field of Search .............. 546/314, 323, 326; 514/354, 355, 357

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |
| 4,895,868 | 1/1990 | Chandraratna | 514/432 |

(List continued on next page.)

FOREIGN PATENT DOCUMENTS 0130795 1/1985 European Pat. Off. .
176034A 4/1986 European Pat. Off. .

(List continued on next page.)

OTHER PUBLICATIONS

CA.95(3): 17978j. Bahner et al, 'Di and Tri-Methoxy Styryl Derivatives of Heterocyclic Nitrogen Compounds', 1981.

(List continued on next page.)

Primary Examiner—Glennon H. Hollrah
Assistant Examiner—Deborah Lambkin
Attorney, Agent, or Firm—Gabor L. Szekeres; Robert J. Baran; Martin A. Voet

[57] ABSTRACT

Compounds of the formula

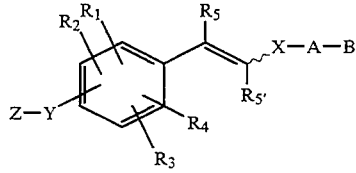

where $R_1$, $R_2$, $R_3$ and $R_4$ independently are hydrogen, lower alkyl of 1 to 6 carbons, halogen or lower alkoxy of 1 to 6 carbons; $R_5$ and $R_5'$ independently are hydrogen or lower alkyl of 1 to 6 carbons; Y is oxygen or sulfur; Z is n-alkyl having 1 to 10 carbons, cyclo or branch-chained alkyl of 3 to 10 carbons, and straight chain alkenyl having 2 to 10 carbons, or cyclo or branched chained alkenyl of 3 to 10 carbons; X is a heteroaryl group selected from a group consisting of thienyl, pyridyl, furyl, pyridazinyl, pyrimidinyl, pyrazinyl, thiazolyl and oxazolyl; A is $(CH_2)_n$ where n is 0-5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds; B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2-5 carbons, have retinoic acid like biological activity.

15 Claims, No Drawings

U.S. PATENT DOCUMENTS

| | | | |
|---|---|---|---|
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |

FOREIGN PATENT DOCUMENTS

| | | |
|---|---|---|
| 0272921 | 6/1988 | European Pat. Off. |
| 0284288 | 9/1988 | European Pat. Off. |
| 0350846 | 7/1989 | European Pat. Off. |
| 3708060 | 9/1987 | Germany |

OTHER PUBLICATIONS

CA105(9): 78843h, Terada et al, 'Herbicidal Phenylpyridyl Ethylenes', 1986.

CA115(9): 91729b, Cushman et al, 'Synthesis and Evaluation of Stilbene and Dihydrostilbene Derivatives as Potential Anti Cancer Agents . . . ', 1991.

CA116(15): 146606n, Cushman et al, 'Synthesis and Evaluation of New Protein-Tyrosine Kinase Inhibitors', 1991.

CA117(5):41413g, Spada et al, 'Cell Proliferation Inhibition with Stynyl-substituted Monoctclic and Bicyckic Getrriaryk Compounds . . . ', 1991.

A General Synthesis of Terminal and Internal Arylalkynes by the Palladium-Catalyzed Reaction of Alkynylzinc Reagents with Aryl Halides by Anthony O. King and Ei-ichi Negishi, *J. Org. Chem.* 43 No. 2, 1978, p. 358.

Conversion of Methyl Ketones into Terminal Acetylenes and (E)-Tri-substituted Olefins of Terpenoid Origin by Ei-ichi, Anthony O. King, and William L. Klima, *J. Org. Chem*, 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 19809, pp. 627–630.

Shudo et al. in *Chem. Phar. Bull.* 33:404–407 (1985).

Kagechika et. al. in *J. Med. Chem.* 31:2182–2192 (1988).

Chemistry and Biology of Snythetic Retinoids by Marcia I. Dawson and William H. Okamura (I), published by CRC Press Inc., 1990, pp. 334–335, 354.

Syntheses of 2,2'-Diacyl-1,1'-biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3-g]isoquinoline Antipsychotics, Gary L. Olson, et al. *American Chemical Society, 1981, Vo. 24, No. 9, pp. 1026–1031.*

6.2.3 Conformational Restriction, Williams, et al., *Drug Discovery and Development,* 1987 The Human Press, pp. 54–55.

V. Retinoid Structure-Biological Activity Relationships, Chemistry and Biology of Synthetic Retinoids, pp. 324–356 (1990), Dawson et al (II).

Davis et al. *J. Organomettalic Chem* 387 (1990) 382–390.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, *The Journal of Investigative Dermatology,* vol. 96, No. 5, May 1991, pp. 792–797.

Organ maintenance of human sebaceous glands: in vitro effects of 13-cis retinoic acid and testosterone, John Ridden, et al., *Journal of Cell Science,* Vo. 95, 1990, pp. 125–136.

Characterization of Human Sebaceous Cells in Vitro, Thomas I. Doran, et al., *The Journal of Investigative Dermatology,* vol. 96, No. 3, Mar. 1991.

*Chemical Abstracts,* vol. 104 (1986) 33961h (Karminski-Zamola et al.

*Hetrocycles* (1985) 23(6) 1497–501.

*Chemical Abstracts* vol. 79 (1973) 18713a.

HETEROARYL SUBSTITUTED PHENYLETHENYL COMPOUNDS HAVING RETINOID-LIKE BIOLOGICAL ACTIVITY

CROSS-REFERENCE TO RELATED APPLICATION

The present application is a divisional of application Ser. No. 07/833,682 filed on Feb. 11, 1992, now abandoned in favor of continuation application Ser. No. 08/126,627.

BACKGROUND OF THE INVENTION

1. Field of the Invention

The present invention is directed to novel compounds which have retinoic acid-like biological activity. More specifically, the present invention relates to compounds having a phenyl substituted ethenyl portion, and a heteroaryl portion. The present invention also relates to pharmaceutical compositions comprising these compounds and to methods of using the compounds and compositions.

2. Related Art

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,723,028 discloses 1,2-diphenylethene (stilbene) derivataves which have retinoic acid-like activity.

U.S. Pat. No. 4,740,519 discloses certain aromatic heterocycle derivatives which have retinoic acid-like activity.

Published European Patent Application 0130795 discloses ethene derivatives, where the ethene moiety is substituted by a substituted phenyl group and by a substituted chroman, thiochroman or quinoline group. The compounds are useful for inhibiting the degradation of cartilage in mammals.

European Patent Application 176034A (published Apr. 2, 1986) discloses tetrahydronaphtalene compounds having an ethynylbenzoic group. U.S. Pat. No. 4,739,098 discloses compounds wherein three olefinic units from the acid-containing moiety of retinoic acid are replaced by an ethynylphenyl functionality. These compound have retinoic acid-like biological activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene (ethyne) group is a substituted phenyl group, and the second substituent is a substituted or unsubstituted 6-chromanyl, 6-thiochromanyl or 6-tetrahydroquinolinyl group. The compounds disclosed and claimed in U.S. Pat. No. 4,810,804 have retinoic acid-like biological activity.

Several co-pending applications and recently issued patents of the present inventor, which are assigned to the assignee of the present application, are directed to further compounds having retinoic acid-like activity.

A published European patent application of the present applicant (Publication No. 0284288, published on Sep. 28, 1988) describes compounds having retinoic acid-like activity which are 4,4 disubstituted chroman-6-yl, 4,4 disubstituted-thiochroman-6-yl acetylenes also substituted by a substituteyd heteroaryl group.

Retinoic acid-like activity has been generally recognized in the art to be associated with useful biological activity. Specifically, compounds having retinoic acid-like activity are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

SUMMARY OF THE INVENTION

This invention covers compounds of Formula 1

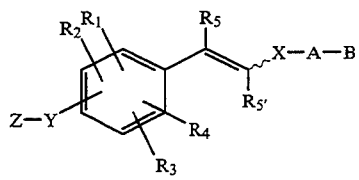

Formula 1 wherein $R_1$, $R_2$, $R_3$ and $R_4$ independently are hydrogen, lower alkyl of 1 to 6 carbons, halogen or lower alkoxy of 1 to 6 carbons;

$R_5$ smf $R_5'$ independently are hydrogen or lower alkyl of 1 to 6 carbons or halogen;

Y is oxygen or sulfur;

Z is n-alkyl having 1 to 10 carbons, cyclo or branch-chained alkyl of 3 to 10 carbons, and straight chain alkenyl having 2 to 10 carbons, or cyclo or branched chained alkenyl of 3 to 10 carbons;

X is a heteroaryl group selected from a group consisting of thienyl, pyridyl, furyl, pyridazinyl, pyrimidinyl, pyrazinyl, thiazolyl and oxazolyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, R12 is lower alkyl, and R13 is divalent alkyl radical of 2-5 carbons.

In a second aspect, this invention relates to the use of the compounds of Formula 1 as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myelorid leukemias, for reversing and preventing atherosclerosis and restenosis resulting from neointiural hyperproliferation, for treating and preventing other non-malignant hyperproliferative diseases such as endometrial hyperplasia, benign prostatic hypertrophy, proliferative vitreal retirropalhy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3

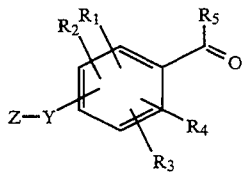

Formula 2

(alkylO)$_2$P(O)CHR'$_5$—X—A—B'   Formula 3 in which R$_1$ through R$_5$, R'$_5$, A, X, Y and Z are defined as in connection with Formula 1, and B' is defined as B in Formula 1 above, or as such a precursor of B which can be readily converted into B by a chemial reaction or reactions well known in the art and within the skill of the practicing organic chemist. The reaction between compounds of Formula 2 and of Formula 3 is conducted under conditions of the Horner-Emmons modification of the Wittig reaction, and the present invention also relates to reactions between the compounds of these formulas and of analogous formulas under Horner-Emmons, Wittig or modified Wittig type conditions to provide the compounds of Formula 1. Furthermore, the present invention also relates to reactions performed on compounds of Formula 1 (or on its precursors) to obtain still further compounds of Formula 1, such reactions including:

homologating a compound of the Formula 1 where A is (CH$_2$)$_n$ and n is 0-4 to give an acid of Formula 1; or converting an acid of Formula 1 to a salt; or
forming an acid addition salt;
converting an acid of Formula 1 to an ester; or
converting an acid of Formula 1 to an amide; or
reducing an acid of Formula 1 to an alcohol or aldehyde; or converting an alcohol of Formula 1 to an ether or ester; or oxidizing an alcohol of Formula 1 to an aldehyde; or
converting an aldehyde of Formula 1 to an acetal; or
converting a ketone of Formula 1 to a ketal.

General Embodiments

Definitions

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

Then term "ester" as used here refers to and covers any compound falling within the definition of that term as classically used in organic chemistry. Where B (of Formula 1) is —COOH, this term covers the products derived from treatment of this function with alcohols, preferably with aliphatic alcohols having 1-6 carbons. Where the ester is derived from compounds where B is —CH$_2$OH, this term covers compounds of the formula —CH$_2$OOCR$_{11}$ where R$_{11}$ is any substituted or unsubstituted aliphatic, aromatic or aliphatic-aromatic group, preferably with 1-6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O—where R$_1$ is lower alkyl of 2-5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain at least one double bond and therefore may have trans and cis (E and Z) isomers. In addition, some of the compounds of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbols $R_1$ through $R_4$ in Formula 1, in the preferred compounds of the present invention these symbols preferably represent hydrogen or lower alkyl groups. Particularly preferred are those compounds where $R_1$ through $R_4$ are all hydrogen and those where the three out of the four of the above-mentioned groups is hydrogen, and one is lower alkyl. Still further preferred among these are compounds where the lower alkyl group is methyl.

With regard to the groups $R_5$ and $R_5'$ in the compounds of Formula 1, compounds are preferred where $R_5$ and $R_5'$ are independently hydrogen or methyl.

The symbol Y represents either oxygen or sulfur in accordance with the present invention.

With regard to the symbol Z in Formula 1, compounds of the invention are preferred where Z represents a branched chain alkyl or branced chain alkenyl group having one double bond. Particularly preferred are compounds where Z represents 3-methyl-2-butenyl.

With regard to the substitution pattern on the phenyl moiety of the compounds of the present invention, compounds are preferred where the Z—Y and ethenyl groups respectively occupy the 1 and 4 or 1 and 3 positions on the phenyl ring (the substitution is para or meta), and where the $R_1$ through $R_4$ groups are hydrogen. Alternatively, compounds are preferred where the Z—Y and ethenyl groups occupy the 1 and 4 or 1 and 3 (para or meta) positions, $R_1$ through $R_3$ are hydrogen, and $R_4$ is methyl and occupies the 6 position (ortho to the etheneyl group).

The symbol X of Formula 1 represents an aromatic heterocylic group which is substituted in the aromatic nucleus by the phenyletheneyl portion and by the A—B moiety of the molecule. The preferred compounds of the invention are those where X represents thiophene, pyridine and furan.

With regard to the side chain (substituent A) on the heteroaryl group X, compounds are preferred where A is $(CH_2)_n$, and still more preferred where n is 0.

With respect to the symbol B, the compounds of the invention are preferred where B is —COOH, or an alkali metal salt or organic amine salt thereof. Alternatively, compounds are preferred where B is respresented by $COOR_8$ (ester where $R_8$ is lower alkyl), $CONR_9R_{10}$ (amide) —$CH_2OH$ (alcohol), $CH_2OCOR_{11}$, $CH_2OR_{11}$ ($R_{11}$ is lower alkyl; lower alkyl esters and ethers formed with a lower alkanol) or B is —CHO or $CH(OR_{12})_2$, $CHOR_{13}O$ (acetal derivatives), where $R_{12}$ and $R_{13}$ are defined as in connection with Formula 1.

The most preferred compounds of the invention are shown in Formula 4:

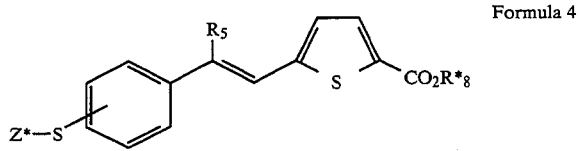

Formula 4

Compound 1 $Z^* = (CH_3)_2C = CH—CH_2—$; $Z^*$—S is in the 3 position; $R_5 = H$ and $R^*_8 =$ ethyl;
Compound 2 $Z^* = (CH_3)_2C = CH—CH_2—$; $Z^*$—S is in the 3 position; $R_5 = H$ and $R^*_8 = H$;
Compound 3 $Z^* = (CH_3)_2C = CH—CH_2—$; $Z^*$—S is in the 4 position; $R_5 = CH_3$ and $R^*_8 =$ ethyl;
Compound 4 $Z^* = (CH_3)_2C = CH—CH_2—$: $Z^*$—S is in the 4 position; $R_5 = CH_3$ and $R^*_8 = H$;
Compound 5 $Z^* = (CH_3)_2C = CH—CH_2—$; $Z^*$—S is in the 3 position; $R_5 = CH_3$ and $R^*_8 =$ ethyl;

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, by *Remington's Pharmaceutical Science*, Edition 17, Mack Publishing Company, Easton, Penn. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation, However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid-like activity of these compounds was confirmed through the classic measure of retionic acid activity involving the effects of retionic acid on ornithine decarboxylase. The original work on the correlation between retinoic acid and decrease in cell proliferation was done by Verma & Boutwell, *Cancer Research,* 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoyl-phorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.,* 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 1, 2 and 3) attained an 80% inhibition of TPA induced ODC activity at the following concentrations ($IC_{80}$):

| Compound | $IC_{80}$ conc (nmols) |
| --- | --- |
| 1 | 147 |
| 2 | 295 |
| 3 | 906 |

Specific Embodiments

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Generally speaking the compounds of the present invention can be prepared by a Wittig or analogous (modified Wittig) reaction between the compounds of Formula 2 and Formula 3, as described above. In this reaction, shown in Reaction Scheme 1, the appropriately substituted phenyl aldehyde or ketone of Formula 2 reacts with the dialkyl (preferably diethyl) phosphonate of Formula 3 derived from the desired heteroaromatic compound, to form an ethene linkage between the substituted phenyl and the substituted heterocyclic moieties of the compounds of the invention. Generally speaking, the Horner Emmons (modified Wittig) reaction is conducted in the presence of a strong base, such as sodium hydride (NaH) or dimsyl sodium (NaCH$_2$SOCH$_3$) in a polar solvent such as dimethylsulfoxide. The coupling of the reagents of Formula 2 and Formula 3 provides the compounds of Formula 1 or of Formula 5.

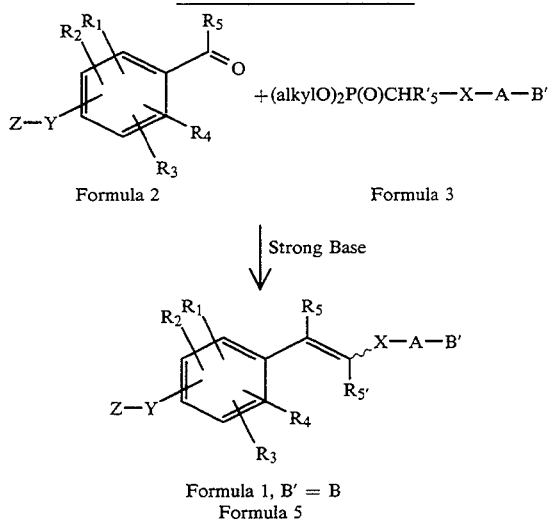

REACTION SCHEME 1

Formula 2    Formula 3

Strong Base

Formula 1, B' = B
Formula 5

The compounds of Formula 5 differ from the compounds of Formula 1 only in that the the symbol B' represents such a group which may be readily converted by reactions well known in the art to a group represented by the symbol B. Compounds of Formula 1 may also be converted to still other compounds represented by Formula 1 with reactions which are known in the art. The A–B and or A–B' functionality of the compounds of Formula 3 can be prepared by well known and published methods of synthetic organic chemistry. By way of example, carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

To increase the value of n before effecting the Wittig (or analogous) coupling reaction of Reaction Scheme 1 (where such compounds are not available from a commercial source) the heteroaromatic derivatives where B is —COOH are subjected to homologation by successive treatment under Arndt-Eistert conditions or other homologation procedures. Alternatively, derivatives where B is different from COOH, may also be homologated by appropriate procedures. The homologated acids can then be esterified by the general procedure outlined in the preceding paragraph.

An alternative means for making compounds where A is (CH$_2$)$_n$ (n is 1–5) is to subject the compounds of Formula 1, where B is an acid or other function, to homologation, using the Arndt-Eistert method referred to above, or other homologation procedures.

Compounds of Formula 1 where A is an alkenyl group having one or more double bonds can be made for example, by having the requisite number of double bonds incorporated into the intermediate of Formula 3. Generally speaking, the compounds of Formula 3 where A is an unsaturated carbon chain can be obtained by synthetic schemes well known to the practicing organic chemist; for example by Wittig and like reactions, or by introduction of a double bond by elimination of halogen from an alpha-halo-heteroarylalkyl-carboxylic acid, ester or like carboxaldehyde. Compounds of Formula 1 where the A group has a triple (acetylenic) bond can be made by using the corresponding intermediate of Formula 3. Such intermediate can be obtained by reactions well known in the art, for example, by reaction of a corresponding heteroaromaticmethyl ketone with strong base, such as lithium diisopropyl amide.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halogenated heteroaromatic compounds, preferably where the halogen is I.

The intermediate compounds of general Formula 2 are prepared in accordance with the generalized reaction steps outlined in Reaction Scheme 2.

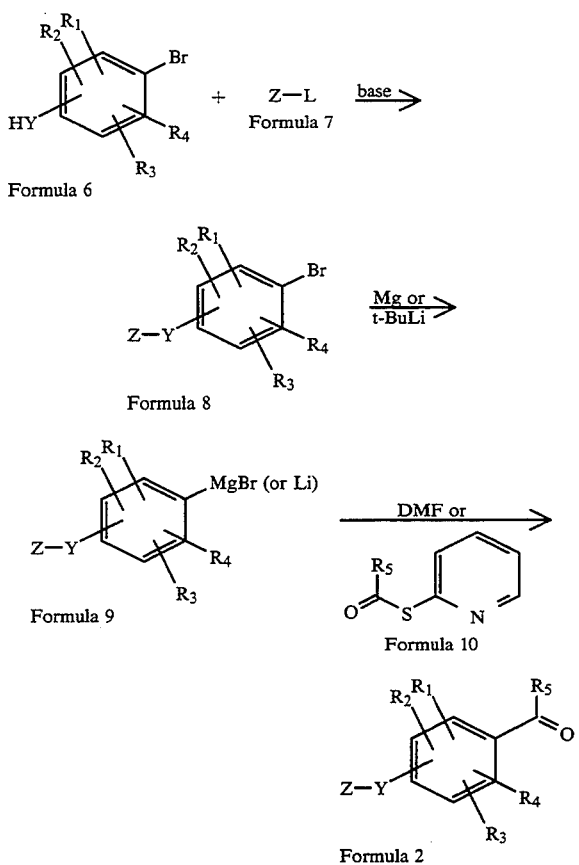

In accordance with this scheme, a halogenated phenol or thiophenol of Formula 6 which has the desired $R_1$ through $R_4$ substituents is the starting material. The general formula indicates a bromo phenol or thiopenol, however instead of bromine another halogen may be used. Examples for the starting material of Formula 6 which are either available commercially, or can be prepared in accordance with reactions well known in the art, are 4-bromothiophenol, 2-methyl-4-bromothiophenol, 4-bromophenol, 2-methyl-4-bromophenol, 3-bromothiophenol and 3-bromophenol.

The compound of Formula 6 is reacted under basic conditions with a compound of the formula Z-L (Formula 7) where Z is defined as in connection with Formula 1, and L symbolizes a leaving group, such as halogen, mesyl, tosyl or the like. Generally speaking, the reaction between the compounds of Formula 6 and Formula 7 is performed under alkylating conditions. The ether or thioether obtained in the foregoing reaction, which is shown by Formula 8, is thereafter converted to a Grignard or like reagent, shown by Formula 9. Specifically, Formula 9 shows a Grignard reagent derived from a bromophenyl alkyl ether or from the bromophenyl alkyl thioether of Formula 8, which is obtained under conditions known in the art for forming Grignard reagents of this type. Alternatively, Formula 9 shows a lithium reagent derived from the bromophenyl alkyl ether or from the bromophenyl alkyl thioether of Formula 8 under conditions of a metal halogen exchange reaction, such as treatment with n-butyllithium. The Grignard or lithium reagent of Formula 9 is thereafter reacted with dimethylformamide to provide the substituted benzaldehyde (Formula 2 where $R_5$ is H), or with a reagent comprising a source for the $R_5$—CO—group, such as the acyl-thiopyridine of Formula 10. An alternative source for the $R_5$—CO group where $R_5$ is methyl, is the reagent N,O-dimethylhydroxylacetamide.

The intermediate compounds of general Formula 3 are prepared in accordance with the generalized reaction steps outlined in Reaction Scheme 3.

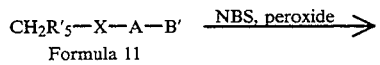
Formula 11

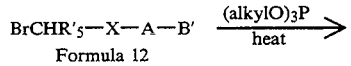
Formula 12

Formula 3

In accordance with Reaction Scheme 3, the heteroaromatic compound of Formula 11 serves as a starting material. This compound bears either the A–B substituent (as the symbols A and B are defined in connection with Formula 1, or the A–B' substituent, wherein B' is defined as in connection with Formula 3. The compound of Formula 11 also bears a methyl group in the position on the heterocycle where the ethene moiety of the compounds of the invention (Formula 1) is attached. The starting materials of Formula 11 are either commercially available or can be obtained in accordance with synthetic procedures known in the art. Commercially available 5-methyl-2-thiophenecarboxylic acid (Aldrich), 2-methylnicotinic acid (Aldrich), 6-methylnicotinic acid (Aldrich), 5-methyl-furan-2-carboxylic acid and 5-methyl-furan-3-carboxylic acid can serve as examples of suitable starting materials for Reaction Scheme 3. The just mentioned starting materials are esterified by any suitable known procedure (such as reaction with ethyl alcohol in the presence of dicyclohexylcarbodiimide (DCC)) and the resulting ester or other intermediate corresponding to Formula 11 is reacted with N-bromosuccinimide and benzoyl peroxide to provide the bromo compound of Formula 12. The compound of Formula 12 is thereafter reacted with a trialkylphosphite (preferably triethylphosphite) to provide the phosphonate of Formula 3.

An alternate synthetic route for making compounds of Formula 1 is the reaction between the phosphonium salt of Formula 13 and the heteroaromatic aldehyde or ketone of Formula 14, as is indicated in Reaction Scheme 4. Still another synthetic route leading to the compounds of Formula 1 is the reaction between the aldehyde or ketone of Formula 15 and the phosphonium salt of Formula 16, as indicated in Reaction Scheme 5. In these formulas and reaction schemes the symbols $R_1$-$R_5$, $R_5'$, Z–Y, X, A and B' are defined as above.

Several other synthetic routes and methods for the preparation of the compounds of the present invention may become readily apparent to those skilled in the art in light of the present disclosure.

Reaction Scheme 4

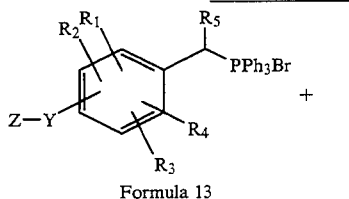
Formula 13

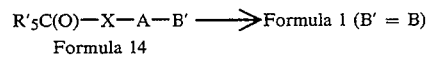
Formula 14

Reaction Scheme 5

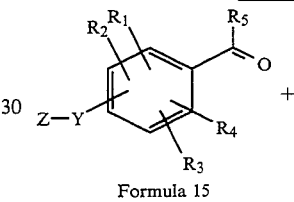
Formula 15

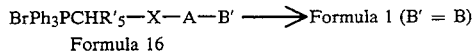
Formula 16

SPECIFIC EXAMPLES 4-(3-Methyl-2-thiobuten-1-yl)bromobenzene (Compound 10)

A mixture of 12.8 g (67.7 mmol) of 4-bromothiophenol and 2.7 g (67.7 mmol) sodium hydroxide in 50 mL acetone was heated to reflux under argon for 2.5 hours. The refluxing mixture was then treated dropwise with a solution of 10.0 g (67.1 mmol) of 4-bromo-2-methyl-2-butene in 10 mL acetone and the mixture heated to reflux for an additional 24 hours. The mixture was then cooled to room temperature and the solvent removed in-vacuo. The residue was treated with 50 mL of water and extracted with 3×75 mL ether.

The ether extracts were combined and washed successively with 3×30 mL of 5% NaOH, 50 mL of water and 50 mL saturated aqueous NaCl and then dried (MgSO$_4$). The solvent was removed in-vacuo and the residual oil purified by Kugelrohr distillation (70° C., 0.1 mm Hg) to give the title compound as a clear, colorless oil.

PMR (CDCl$_3$): δ1.58 (3H, s), 1.70 (3H, s), 3.50 (2H, d, J=8.3 Hz), 7.36 (2H, d, J=8.3 Hz).

2-Bromo-5-(3-methyl-2-thiobuten-1yl)toluene (Compound 11).

A mixture of 5.0 g (24.6 mmol) of 4-bromo-2-methyl-thiophenol (Fairfield Chemical Co.) and 1.08 g (27.1 mmol) sodium hydroxide in 25 mL acetone was heated to reflux under argon for 2.5 hours. The refluxing mixture was then treated dropwise with a solution of 3.12 mL (27.1 mmol) of 4-bromo-2-methyl-2-butene in 5 mL acetone and the mixture heated to reflux for an additional 24 hours. The mixture was then cooled to room temperature and the solvent removed in-vacuo. The residue was treated with 25 mL of water and extracted with 3×40 mL ether.

The ether extracts were combined and washed successively with 3×15 mL of 5% NaOH, 25 mL of water and 25 mL saturated aqueous NaCl and then dried (MgSO$_4$). The solvent was removed in-vacuo and the residual oil purified by Kugelrohr distillation (125° C., 1.5 mm Hg) to give the title compound as a clear, colorless oil.

PMR (CDCl$_3$): δ1.60 (3H, s), 1.71 (3H, s), 2.35 (3H, s), 3.51 (2H, d, J=7.8 Hz), 5.27 (1H, t, J=7.8 Hz), 7.02 (1H, dd, J=2.4, 8.3 Hz), 7.18 (1H, d, J=2.4 Hz), 7.40 (1H, d, J=8.3 Hz).

(3-Methyl-2-thiobuten-1-yl)bromobenzene (Compound 12)

A mixture of 5.0 g (24.6 mmol) of 3-bromothiophenol and 1.08 g (27.1 mmol) sodium hydroxide in 25 mL acetone was heated to reflux under argon for 2.5 hours. The refluxing mixture was then treated dropwise with a solution of 3.12 mL (27.1 mmol) of 4-bromo-2-methyl-2-butene in 5 mL acetone and the mixture heated to reflux for an additional 24 hours. The mixture was then cooled to room temperature and the solvent removed in-vacuo. The residue was treated with 25 mL of water and extracted with 3×40 mL ether.

The ether extracts were combined and washed successively with 3×15 mL of 5% NaOH, 25 mL of water and 25 mL saturated aqueous NaCl and then dried (MgSO$_4$). The solvent was removed in-vacuo and the residual oil purified by Kugelrohr distillation (125° C., 1.5 mm Hg) to give the title compound as a clear, colorless oil.

PMR (CDCl$_3$): δ1.62 (3H, s), 1.73 (3H, s), 3.54 (2H, d, J=7.8 Hz), 5.28 (1H, t, J=7.8 Hz), 7.12 (1H, dd, J=7.1, 7.1 Hz), 7.23 (1H, ddd, J=0.7, 1.7, 7.1 Hz), 7.29 (1H, dd, J=0.7, 1.7, 7.1 Hz), 7.44 (1H, dd, J=0.7, 1.7 Hz).

4-(3-Methyl-2-thiobuten-1-yl)benzaldehyde (Compound 13)

To a solution of 1.,9517 g (7.5886 mmol) of 4-(3-methyl-2-thiobuten-1-yl)bromobenzene (Compound 10) in 25 ml dry ether at −78° C. under argon, was added dropwise 9.0 ml of 1.7M (15.3 mmol) tert-butyllithium in pentane. The reaction mixture was stirred at −78° C. for 3 hours and then treated dropwise with a solution of 885.7 mg (12.12 mmol) of dimethylformamide in 6 ml dry ether. The cooling bath was then removed and the mixture stirred at room temperature for 26 hours, then cooled to 0° C. and treated with 75 ml of saturated NH$_4$Cl. This mixture was then extracted with 3×75 ml ether. The ether extracts were combined and washed successively with saturated NaHCO$_3$ and saturated NaCl solutions and then dried (MgSO$_4$). The solvent was then removed in-vacuo and residue purified by flash chromatography (silica; 10% ethyl acetate in hexanes) followed by Kugelrohr distillation (90° C., 0.25 mm) to give the title compound as a colorless oil.

PMR (CDCl$_3$: δ1.74 (3H, s), 1.76 (3H, s), 3.66 (2H, d, J∼6.9 Hz), 5.33 (1H, t, J∼6.9 Hz), 7.35 (2H, d, J∼8.8 Hz), 7.76 (2H, d J∼8.8 Hz), 9.92 (1H, s).

2-Methyl-4-(3-methyl-2-thiobuten-1-yl)benzaldehyde (Compound 14)

To a −78° C. solution of 0.5 g (1.84 mmol) of 2-bromo-5-(3-methyl-2-thiobuten-1-yl)toluene (Compound 11) and 8 mL THF under argon was added dropwise 0.81 mL of a 2.5M solution of n-butyllithium and hexane (2.02 mmol). After 15 minutes, 2.2 mL (15.4 mmol) of N,N-dimethylformamide was added dropwise and the solution was allowed to warm to 0° C. in an ice-water bath and stirred for an additional hour. The solution was treated with 5 mL of water and extracted with 3×25 mL ether.

The ether extracts were combined and washed with 25 mL saturated aqueous NaCl and then dried (MgSO$_4$). The solvent was removed in-vacuo and the residual oil purified by flash chromatography (SiO$_2$, 95:5, hexane:ethyl acetate) to give the title compound as a clear, colorless oil.

PMR (CDCl$_{13}$): δ1.73 (3H, s), 1.75 (3H, s) 2.63 (3H, s), 3.63 (2H, d, J=7.8 Hz), 5.31 (1H, t, J=7.8 Hz), 7.09 (1H, d, J=1.7 Hz), 7.19 (1H, dd, J=1.7, 8.2 Hz), 7.68 (1H, dd, J=8.2 Hz), 10.16 (1H, s)

3-(3-methyl-2-thiobuten-1-yl)benzaldehyde (Compound 15)

To a −78° C. solution of 1.5 g (5.83 mmol) of 3-(3-methyl-2-thiobuten-1-yl)bromobenzene (Compound 12) and 25 mL THF under argon was added dropwise 2.56 mL of a 2.5M solution of n-butyllithium and hexane (5.83 mmol). After 15 minutes, 7.0 mL (87.8 mmol) of N,N-dimethylformamide was added dropwise and the solution was allowed to warm to 0° C. in an ice-water bath and stirred for an additional hour. The solution was treated with 15 mL of water and extracted with 3×75 Ml ether.

The ether extracts were combined and washed with 75 mL saturated aqueous NaCl and then dried (MgSO$_4$). The solvent was removed in-vacuo and the residual oil purified by flash chromatography (SiO$_2$, 95:5, hexane:ethyl acetate) to give the title compound as a clear, colorless oil.

PMR (CDCl$_3$): δ1.63 (3H, s), 1.73 (3H, s), 3.60 (2H, d, J=7.7 Hz), 5.30 (1H, t, J=7.7 Hz), 7.43 (1H, dd, J=7.6, 7.6 Hz), 7.56 (1H, dd, J=2.0, 3.3 Hz), 7.65 (1H, dd, J=1.5, 7.6 Hz), 7.80 (1H, d, J=1.5 Hz), 9.97 (1H, s).

2-Pyridylthioacetate (Compound 16)

A solution of 12.5 mL (90 mmol) of triethylamine, 27 mg dimethylaminopyridine and 13 mL dichloromethane was added dropwise to a solution of 5 g (44.5 mmol) of 2-pyridinethiol and dichloromethane (130 mL) at 0° C. under argon. After 5 minutes, 4.16 mL (58.5 mmol) of acetyl chloride was added dropwise and the solution was stirred at 0° C. for 30 minutes and then at room temperature for 3 hours. The solution was treated with 10 mL of 10% aqueous HCl and the layers were separated.

The organic layer was washed with 100 mL water, 100 mL saturated aqueous NaHCO$_3$, 100 mL saturated aqueous NaCl and then dried (MgSO$_4$). The solvent was removed in-vacuo and the residual oil purified by bulb-to bulb distillation (bp=90° C., 2 mm Hg)) to give the title compound as a clear, yellow oil.

PMR (CDCl$_3$): δ2.50 (3H, s), 7.30 (1H, dd, J=4.9, 7.4 Hz), 7.62 (1H, d, J=8.3 Hz), 7.75 (1H, dd, J=5.9, 7.8 Hz), 8.62 (1H, dd, J=2, 4.9 Hz).

4-(3-methyl-2-thiobuten-1-yl)acetophenone (Compound 17)

A solution of 1.29 g (5.0 mmol) of 4-(3-methyl-2-thiobuten-1-yl)bromobenzene (Compound 10) and 2.5 mL THF was added to 0.134 g of magnesium turnings under argon. The solution was heated to initiate the reaction and then 2.5 mL of THF was added and the suspension stirred at reflux for an hour. The resulting solution was cooled to room temperature and transferred via cannula to an ice-cold solution of 0.77 g (5.0 mmol) of 2-pyridylthioacetate (Compound 16) and 5 mL THF. After 30 minutes, the solution was treated with 1.0 mL of water and concentrated under reduced pressure. The residue was extracted with 3×10 mL ether.

The ether extracts were combined and washed with 10 mL saturated aqueous NaCl and then dried (MgSO₄). The solvent was removed in-vacuo and the residual oil purified by flash chromatography (SiO₂, 95:5, hexane:ethyl acetate) to give the title compound as a white solid.

PMR (CDCl₃): δ1.71 (3H, s), 1.74 (3H, s), 2.57 (3H, s), 3.63 (2H, d, J=7.4 Hz), 5.31 (1H, t, J=7.4 Hz), 7.31 (2H, d, J=8.5 Hz), 7.86 (2H, d, J=8.5 Hz).

2-Methyl-4-(3-methyl-2-thiobuten-1-yl)acetophenone (Compound 18)

A solution of 1.36 g (5.0 mmol) of 2-bromo-5-(3-methyl-2-thiobuten-1-yl)toluene (Compound 11) and 2.5 mL THF was added to 0.134 g of magnesium turnings under argon. The solution was heated to initiate the reaction and then 2.5 mL of THF was added and the suspension stirred at reflux for an hour. The resulting solution was cooled to room temperature and transferred via cannula to an ice-cold solution of 0.77 g (5.0 mmol) of 2-pyridylthioacetate (Compound 16) and 5 mL THF. After 30 minutes, the solution was treated with 1.0 mL of water and concentrated under reduced pressure. The residue was extracted with 3×10 mL ether.

The ether extracts were combined and washed with 10 mL saturated aqueous NaCl and then dried (MgSO₄). The solvent was removed in-vacuo and the residual oil purified by flash chromatography SiO₂, 95:5, hexane:ethyl acetate) to give the title compound as a clear, pale yellow oil.

PMR (CDCl₃): δ1.70 (3H, s), 1.74 (3H, s), 2.53 (3H, s), 2.56 (3H, s), 3.61 (2H, d, J=7.8 Hz), 5.31 (1H, t, J=7.8 Hz), 7.11 (1H, s), 7.13 (1H, d, J=8.0 Hz), 7.65 (1H, d, J=8.0 Hz).

3-(3-methyl-2-thiobuten-1-yl)acetophenone (Compound 19)

To a −78° C. solution of 1.5 g (5.83 mmol) of 3-(3-methyl-2-thiobuten-1-yl)bromobenzene (Compound 12) and 25 mL THF under argon was added dropwise 2.56 mL of a 2.5M solution 5.83 mmol) of n-butyllithium and hexane. After 15 minutes, 0.57 g (5.52 mmol) of N,O-dimethylhydroxylacetamide was added dropwise and the solution was allowed to warm to 0° C. in an ice-water bath and stirred for an additional hour. The solution was treated with 15 mL of dilute HCl and extracted with 3×75 mL ether.

The ether extracts were combined and washed with 75 mL saturated aqueous NaCl and then dried (MgSO₄). The solvent was removed in-vacuo and the residual oil purified by flash chromatography (SiO₂, 95:5, hexane:ethyl acetate) to give the title compound as a clear, pale yellow oil.

PMR (CDCl₃): δ1.61 (3H, s), 1.72 (3H, s), 2.59 (3H, s), 3.58 (2H, d, J=7.7 Hz), 5.30 (1H, t, J=7.7 Hz), 7.36 (1H, dd, J=7.7, 7.7 Hz), 7.50 (1H, d, J=7.7 Hz), 7.74 (1H, d, J=7.7 Hz), 7.89 (1H, s).

Ethyl 5-methyl-2-thiophenecarboxylate (Compound 20)

To a stirred solution of 15.9 g (77.4 mmol) of 1,3-dicyclohexylcarbodiimide in 40 mL dichloromethane was added 10 g (70.3 mmol) of 5-methyl-2-thiophenecaboxylic acid and 4.85 g (105.5 mmol) of anhydrous ethanol. 0.86 g of dimethylaminopyridine was then added and the suspension stirred at room temperature for 20 hours.

The resulting white precipitate was removed by filtration. The filtrate was washed with water, dried (MgSO₄), filtered and concentrated under reduced pressure. The residue was purified by bulb-to-bulb distillation (bp=95° C. 3 mm Hg) to give the title compound as a clear, pale yellow oil.

PMR (CDCl₃): δ1.36 (3H, t, J=7.1 Hz), 2.52 (3H, s), 4.32 (2H, q, J=7.1 Hz), 6.76 (1H, d, J=3.8 Hz), 7.61 (1H, d, J=3.8 Hz).

Ethyl 5-bromomethyl-2-thiophenecarboxylate (Compound 21)

N-Bromosuccinimide (23.5 g, 132 mmol), benzoyl peroxide (0.26 g) and 90 mL of benzene were brought to reflux under argon. Ethyl 5-methyl-2-thiophenecarboxylate (Compound 20, 22.5 g, 132 mmol) was added dropwise through an addition funnel and the resulting mixture was refluxed for 6 hours and then cooled to room temperature and stirred for 16 hours. The mixture was treated with 50 mL of water and extracted with 3×75 mL ether.

The ether extracts were combined and washed with 75 mL saturated aqueous NaCl and then dried (MgSO₄). The solvent was removed in-vacuo and the residual oil purified by flash chromatography (SiO₂, 99:1, hexane:ethyl acetate) to give the title compound as a clear, yellow oil.

PMR (CDCl₃): δ1.37 (3H, t, J=7.3 Hz), 4.35 (2H, q, J=7.3 Hz), 4.68 (3H, s), 7.09 (1H, d, J=4.0 Hz), 7.64 (1H, d, J=4.0 Hz).

Diethyl (2-carboethoxy-5-thiophenyl)methylphosphonate (Compound 22)

A mixture of 4.99 g (20.0 mmol) of ethyl 5-bromomethyl-2-thiophenecarboxylate (Compound 21) and 5.17 mL (30.0 mmol) of triethylphophite was heated to 120° C. under argon for 6 hours and the excess triethylphosphite removed by distillation.

The product was purified by vacuum distillation (bp=175°, 3 mm Hg) to give the title compound as a clear, pale yellow oil.

PMR (CDCl₃): δ1.30 (6H, t, J=7.1 Hz), 1.37 (3H, t, J=7.2 Hz), 3.38 (2H, d, J=20.9 Hz), 4.05–4.15 (4H,m), 4.33 (2H, q, J=7.1 Hz), 6.99 (1H, dd, J=3.6, 3.6 Hz), 7.66 (1H, d, J=1.1, 3.6 Hz).

5-(E-2-(3-(3-methyl-2-thiobuten-1-yl)phenyl)ethenyl)-2-thiophenecarboxylate (Compound 1)

400 mg of 60% NaH in mineral oil was washed successively with three 5-mL portions of hexane. The residual hexane was removed under vacuum and the vacuum was broken with dry argon. 10 ml of dimethyl sulfoxide (DMSO) was added and the resulting suspension was heated to 60° C. for 1 hour to produce a 1M solution of dimsyl sodium. 2.0 mL of 1M dimsyl sodium was added to 0.674 g (2.2 mmol) of diethyl 2-carboethoxy-5-thiophenylmethylphosphonate (Compound 22) and the resulting rust-colored solution was stirred for 30 minutes at room temperature under argon. This solution was added to 0.220 g (1.0 mmol) of 3-(3-methyl-2-thiobuten-1-yl)benzaldehyde (Compound 15) and 3.5 mL DMSO and this solution was stirred for an additional 2.5 hours. The mixture was treated with 10 mL of water and extracted with 3×25 mL ether.

The ether extracts were combined and washed with 25 mL saturated aqueous NaCl and then dried (MgSO₄). The solvent was removed in-vacuo and the residual oil purified by flash chromatography (SiO₂, 95:5, hexane:ethyl acetate) to give the title compound as a light yellow solid. A small portion was recrystallized from ethanol).

PMR (CDCl$_3$): δ1.38 (3H, t, J=7.2 Hz), 1.61 (3H, s), 1.73 (3H, s), 3.57 (2H, d, J=7.7 Hz), 4.35 (2H, q, J=7.2 Hz), 5.31 (1H, t, J=7.7 Hz), 6.98 (1H, d, J=16.1 Hz), 7.04 (1H, d, J=3.9 Hz), 7.15 (1H, d, J=16.1 Hz), 7.26 (3H, m), 7.42 (1H, s), 7.68 (1H, d, J=3.9 Hz).

Ethyl 5-(E-2-(4-(3-methyl-2-thiobuten-1-yl)phenyl) propen-1-yl)-2-thiophencarboxlate (Compound 3)

400 mg of 60% NaH in mineral oil was washed successively with three 5-mL portions of hexane. The residual hexane was removed under vacuum and the vacuum was broken with dry argon. 10 ml of dimethyl sulfoxide (DMSO) was added and the resulting suspension was heated to 60° C. for 1 hour to produce a 1M solution of dimsyl sodium. 1.36 mL of dimsyl sodium was added to 0.46 g (1.5 mmol) of diethyl 2-carboethoxy-5-thiophenylmethylphosphonate (Compound 22) and the resulting rust-colored solution was stirred for 30 minutes at room temperature under argon. This solution was added to 0.15 g (0.68 mmol) of 4-(3-methyl-2-thiobutenyl)acetophenone (Compound 17) and 2.4 mL DMSO and this solution was stirred for an additional 2.0 hours. The solution was treated with 0.41 mL of a 2.0M solution of NaOEt and EtOH and the solution stirred an additional 2 hours at room temperature. The mixture was poured into 40 mL of 5% aq. NaHCO$_3$ and extracted with 5×25 mL ether.

The ether extracts were combined and washed with 25 mL saturated aqueous NaCl and then dried (MgSO$_4$). The solvent was removed in-vacuo and the residual oil purified by flash chromatography (SiO$_2$, 98:2, hexane:ethyl acetate) to give the title compound as a light yellow solid.

PMR (CDCl$_3$): δ1.36(3H, t, J=7.1 Hz), 1.63 (3H, s), 1.73 (3H, s), 2.41 (3H, s), 3.57 (2H, d, J=7.3 Hz), 4.36 (2H, q, J=7.1 Hz), 5.31 (1H, t, J=7.3 Hz), 6.92 (1H, s), 7.04 (1H, d, J=4.0), 7.32 (2H, d, J=8.6 Hz), 7.40 (2H, d, J=8.6 Hz), 7.73 (1H, d, J=4.0 Hz).

Ethyl 5-(E-2-(3-(3-methyl-2-thiobuten-1-yl)phenyl)propen-1-yl)-2-thiophencarboxylate (Compound 5)

400 mg of 60% NaH in mineral oil was washed successively with three 5-mL portions of hexane. The residual hexane was removed under vacuum and the vacuum was broken with dry argon. 10 ml of dimethyl sulfoxide (DMSO) was added and the resulting suspension was heated to 60° C. for 1 hour to produce a 1M solution of dimsyl sodium. 2.0 mL of dimsyl sodium was added to 0.674 g (2.2 mmol) of diethyl 2-carboethoxy-5-thiophenmethylphosphonate (Compound 22) and the resulting rust-colored solution was stirred for 30 minutes at a room temperature under argon. This solution was added to 0.220 g (1.0 mmol) of 3-(3-methyl-2-thiobuten-1-yl)acetophenone (Compound 19) and 3.5 mL DMSO and this solution was stirred for an additional 2.0 hours. The solution was treated with 0.60 mL of a 2.0M solution of NaOEt and EtOH and the solution stirred an additional 12 hours at room temperature. The mixture was poured into 10 mL of 1% aq. HCl and extracted with 5×25 mL ethyl acetate.

The ethyl acetate extracts were combined and washed with 25 mL saturated aqueous NaCl and then dried (MgSO$_4$). The solvent was removed in-vacuo and the residual oil purified by flash chromatography (SiO$_2$, 95:5, hexane:ethyl acetate) to give the E- and Z-isomers as an inseparable mixture in a ratio of 85:15, respectively. The isomers were separated by HPLC (3% ethyl acetate in hexane) to give the title compound.

PMR (CDCl$_3$): δ1.39 (3H, t, J=7.1 Hz), 1.60 (3H, s), 1.72 (3H, s), 2.41 (3H, s), 3.57 (2H, d, J=7.7 Hz), 4.35 (2H, q, J=7.1 Hz), 5.31 (1H, t, J=7.7 Hz), 6.89 (1H, s), 7.04 (1H, d, J=4.0 Hz), 7.25–7.43 (3H, m), 7.43 (1H, s), 7.73 (1H, d, J=4.0 Hz).

5-(E-2-(3-(3-methyl-2-thiobuten-1-yl)phenyl)ethenyl)-2-thiophenecarboxylic acid (Compound 2)

To a solution of 141 mg of ethyl 5-(E-2-(3-(3-methyl-2-thiobuten-1-yl)phenyl)ethenyl)-2-thiophenecarboxylate (Compound 1) in 4 mL of ethanol under argon was added dropwise 1 mL of a 2N solution of aqueous potassium hydroxide. The solution was stirred at room temperature for 18 hours, cooled in an ice-water bath and acidified with 3N aqueous hydrochloric acid. The resulting precipitate was extracted into ether, the layers separated and the ether layer washed with saturated aqueous sodium chloride, dried (MgSO$_4$), and concentrated under reduced pressure. The resulting solid was recrystallized from ethanol to give the title compound.

PMR (CDCl$_3$): δ1.61 (3H, s), 1.73 (3H, s), 3.57 (2H, d, J=7.7 Hz), 5.31 (1H, t, J=7.7 Hz), 7.02 (1H, d, J=15.9 Hz), 7.08 (1H, d, J=3.7 Hz), 7.17 (1H, d, J=15.9 Hz), 7.78 (1H, d, J=3.7 Hz).

5-(E-2-(4-(3-methyl-2-thiobuten-1-yl)pheny)propen-1yl)-2-thiophencarboxylic acid (Compound 4)

To a solution of 40 mg of ethyl 5-(E-2-(4-(3-methyl-2-thiobuten-1-yl)phenyl)propen 1yl)-2-thiophencarboxylate (Compound 3) in 3 mL of ethanol under argon was added dropwise 1 mL of a 2N solution of aqueous potassium hydroxide. The solution was stirred at room temperature for 18 hours, cooled in an ice-water bath and acidified with 3N aqueous hydrochloric acid. The resulting precipitate was extracted into ether, the layers separated and the ether layer washed with saturated aqeous sodium chloride, dried (MgSO$_4$), and concentrated under reduced pressure. The resulting solid was recrystallized from ethanol to give the title compound.

PMR (D$^6$-acetone): δ1.64 (3H, s), 1.70 (3H, s), 2.41 (3H, s), 3.63 (2H, d, J=7.4 Hz), 5.30 (1H, t, J=7.4 Hz), 7.13 (1H, s), 7.25 (1H, d, J=3.9 Hz), 7.35 (2H, d, J=8.5 Hz), 7.53 (2H, d, J=8.5 Hz), 7.75 (1H, d, J=3.9 Hz).

The following further examplary compounds of the invention can be prepared in an analogous manner by the Wittig reaction (coupling) of the following intermediates:

E and Z ethyl 2-(4-(3-methyl-2-thiobuten-1-yl)phenyl)ethenyl)-3-pyridinecarboxylate from 4-(3-methyl-2-thiobuten-1-yl)benzaldehyde and diethyl (3-carboethoxy-2-pyridyl)methylphosphonate;

E and Z ethyl 2-(3-(3-methyl-2-thiobuten-1-yl)phenyl)ethenyl)-3-pyridinecarboxylate from 3-(3-methyl-2-thiobuten-1-yl)benzaldehyde and diethyl (3-carboethoxy-2-pyridyl)methylphosphonate;

E and Z ethyl 2-(4-(3-methyl-2-thiobuten-1-yl)-2-methylphenyl)ethenyl)-3-pyridinecarboxylate from 4-(3-methyl-2-thiobuten-1-yl)-2-methylbenzaldehyde and diethyl (3-carboethoxy-2-pyridyl)methylphosphonate;

E and Z ethyl 2-(3-(3-methyl-2-thiobuten-1-yl)-2-methylphenyl)ethenyl)-3-pyridinecarboxylate from 3-(3-methyl-2-thiobuten-1-yl)-2-methylbenzaldehyde and diethyl (3-carboethoxy-2-pyridyl)methylphosphonate;

E and Z ethyl 2-(4-(3-methyl-2-thiobuten-1-yl)-phenyl)-propen-1-yl)-3-pyridinecarboxylate from 4-(3-methyl-2-thiobuten-1-yl)acetophenone and diethyl (3-carboethoxy-2-pyridyl)methylphosphonate;

E and Z ethyl 2-(3-(3-methyl-2-thiobuten-1-yl)phenyl)-propen-1-yl)-3-pyridinecarboxylate from 3-(3-methyl-2-thiobuten-1-yl)acetophenone and diethyl (3-carboethoxy-2-pyridyl)methylphosphonate;

E and Z ethyl 2-(4-(3-methyl-2-thiobuten-1-yl)-2-methylphenyl)propen-1-yl)-3-pyridinecarboxylate from 4(3-methyl-2-thiobuten-1-yl)-2-methylacetophenone and diethyl (3-carboethoxy-2-pyridyl)methylphosphonate;

E and Z ethyl 2-(3-(3-methyl-2-thiobuten-1-yl)-2-methylphenyl)propen-1-yl)-3-pyridinecarboxylate from 3-(3-methyl-2-thiobuten-1-yl)-2-methylacetophenone and diethyl (3-carboethoxy-2-pyridyl)methylphosphonate;

E and Z ethyl 2-(4-(3-methyl-2-thiobutenyl)phenyl)ethenyl)-5-pyridinecarboxylate from 4-(3-methyl-2-thiobuten-1-yl)benzaldehyde and diethyl (5-carboethoxy-2-pyridyl)methylphosphonate;

E and Z ethyl 2-(3-(3-methyl-2-thiobutenyl)phenyl)ethenyl)-5-pyridinecarboxylate from 3-(3-methyl-2-thiobuten-1-yl)benzaldehyde and diethyl (5-carboethoxy-2-pyridyl)methylphosphonate;

E and Z ethyl 2-(4-(3-methyl-2-thiobuten-1-yl)-2-methylphenyl)ethenyl)-5-pyridinecarboxylate from 4-(3-methyl-2-thiobuten-1-yl)-2-methylbenzaldehyde and diethyl (5-carboethoxy-2-pyridyl)methylphosphonate;

E and Z ethyl 2-(3-(3-methyl-2-thiobuten-1-yl)-2-methylphenyl)ethenyl)-5-pyridinecarboxylate from 3-(3-methyl-2-thiobuten-1-yl)-2-methylbenzaldehyde and diethyl (5-carboethoxy-2-pyridyl)methylphosphonate;

E and Z ethyl 2-(4-(3-methyl-2-thiobuten-1-yl)-phenyl)-propen-1-yl)-5-pyridinecarboxylate from 4-(3-methyl-2-thiobuten-1-yl)acetophenone and diethyl (5-carboethoxy-2-pyridyl)methylphosphonate;

E and Z ethyl 2-(3-(3-methyl-2-thiobuten-1-yl)-phenyl)-propen-1-yl)-5-pyridinecarboxylate from 3-(3-methyl-2-thiobuten-1-yl)acetophenone and diethyl (5-carboethoxy-2-pyridyl)methylphosphonate;

E and Z ethyl 2-(4-(3-methyl-2-thiobuten-1-yl)-2-methylphenyl)propen-1-yl)-5-pyridinecarboxylate from 4-(3-methyl-2-thiobuten-1-yl)-2-methylacetophenone and diethyl (5-carboethoxy-2-pyridyl)methylphosphonate;

E and Z ethyl 2-(3-(3-methyl-2-thiobuten-1-yl)-2-methylphenyl)propen-1-yl)-5-pyridinecarboxylate from 3-(3-methyl-2-thiobuten-1-yl)-2-methylacetophenone and diethyl (5-carboethoxy-2-pyridyl)methylphosphonate;

E and Z ethyl 2-(4-(3-methyl-2-thiobuten-1-yl)phenyl)ethenyl)-5-furancarboxylate from 4-(3-methyl-2-thiobuten-1-yl)benzaldehyde and diethyl (5-carboethoxy-2-furyl)methylphosphonate;

E and Z ethyl 2-(3-(3-methyl-2-thiobuten-1-yl)phenyl)ethenyl)-5-furancarboxylate from 3-(3-methyl-2-thiobuten-1-yl)benzaldehyde and diethyl (5-carboethoxy-2-furyl)methylphosphonate;

E and Z ethyl 2-(4-(3-methyl-2-thiobuten-1-yl)-2-methylphenyl)ethenyl)-5-furancarboxylate from 4-(3-methyl-2-thiobuten-2-yl)-2-methylbenzaldehyde and diethyl (5-carboethoxy-2-furyl)methylphosphonate;

E and Z ethyl 2-(3-(3-methyl-2-thiobuten-1-yl)-2-methylphenyl)ethenyl)-5-furancarboxylate from 3-(3-methyl-2-thiobuten-1-yl)-2-methylbenzaldehyde and diethyl (5-carboethoxy-2-furyl)methylphosphonate;

E and Z ethyl 2-(4-(3-methyl-2-thiobuten-1-yl)phenyl)-propen-1-yl)-5-furancarboxylate from 4-(3-methyl-2-thiobuten-1-yl)acetophenone and diethyl (5-carboethoxy-2-furyl)methylphosphonate;

E and Z ethyl 2-(3-(3-methyl-2-thiobuten-1-yl)phenyl)-propen-1-yl)-5-furancarboxylate from 3-(3-methyl-2-thiobuten-1-yl)acetophenone and diethyl (5-carboethoxy-2-furyl)methylphosphonate;

E and Z ethyl 2-(4-(3-methyl-2-thiobuten-1-yl)-2-methylphenyl)propen-1-yl)-5-furancarboxylate from 4-(3-methyl-2-thiobuten-1-yl)-2-methylacetophenone and diethyl (5-carboethoxy-2-furyl)methylphosphonate;

E and Z ethyl 2-(3-(3-methyl-2-thiobuten-1-yl)-2-methylphenyl)propen-1-yl)-5-furancarboxylate from 3-(3-methyl-2-thiobuten-1-yl)-2-methylacetophenone and diethyl (5-carboethoxy-2-furyl)methylphosphonate;

E and Z ethyl 2-(4-(3-methyl-2-thiobuten-1-yl)phenyl)ethenyl)-4-furancarboxylate from 4-(3-methyl2-thiobuten-1-yl)benzaldehyde and diethyl (4-carboethoxy-2-furyl)methylphosphonate;

E and Z ethyl 2-(3-(3-methyl-2-thiobutenyl)phenyl)ethenyl)-4-furancarboxylate from 3-(3-methyl-2-thiobuten-1-yl)benzaldehyde and diethyl (4-carboethoxy-2-furyl)methylphosphonate;

E and Z ethyl 2-(4-(3-methyl-2-thiobuten-1-yl)-2-methylphenyl)ethenyl)-4-furancarboxylate from 4-(3-methyl-2-thiobuten-1-yl)-2-methylbenzaldehyde and diethyl (4-carboethoxy-2-furyl)methylphosphonate;

E and Z ethyl 2-(3-(3-methyl-2-thiobuten-1-yl)-2-methylphenyl)ethenyl)-4-furancarboxylate from 3-(3-methyl-2-thiobuten-1-yl)-2-methylbenzaldehyde and diethyl (4-carboethoxy-2-furyl)methylphosphonate;

E and Z ethyl 2-(4-(3-methyl-2-thiobuten-1-yl)-phenyl)-propen-1-yl)-4-furancarboxylate from 4-(3-methyl-2-thiobuten-2-yl)acetophenone and diethyl (4-carboethoxy-2-furyl)methylphosphonate;

E and Z ethyl 2-(3-(3-methyl-2-thiobuten-1-yl)phenyl)-propen-1-yl)-4-furancarboxylate from 3-(3-methyl-2-thiobuten-1-yl)acetophenone and diethyl (4-carboethoxy-2-furyl)methylphosphonate;

E and Z ethyl 2-(4-(3-methyl-2-thiobutenyl)-2-methylphenyl)propen-1-yl)-4-furancarboxylate from 4-(3-methyl-2-thiobuten-1-yl)-2-methylacetophenone and diethyl (4-carboethoxy-2-furyl)methylphosphonate;

E and Z ethyl 2-(3-(3-methyl-2-thiobutenyl)-2-methylphenyl)propen-1-yl)-4-furancarboxylate from 3-(3-methyl-2-thiobuten-1-yl)-2-methylacetophenone and diethyl (4-carboethoxy-2-furyl)methylphosphonate.

Substituting respectively, diethyl (3-carboethoxy-6-pyridazyl)methylphosphonate, diethyl (5-carboethoxy-6-pyrimidyl)methylphosphonate, diethyl (5-carboethoxy-2-pyrazyl)methylphosphonate, diethyl (2-carboethoxy-4-thiazolyl)methylphosphonate and diethyl (2-carboethoxy-4-oxazolyl)methylphosphonate for diethyl (3-carboethoxy-2-pyridyl)methylphosphonate in the above-listed reactions the corresponding pyridazinyl, pyrimidyl, parazinyl, thiazolyl and oxazolyl derivatives are obtained.

What is claimed is:

1. A process of treating a mammal for the purpose of preventing, curing, alleviating or reversing the diseases or conditions selected from the group consisting of acne, Darier's disease, psoriasis, icthyosis, eczema, atopic dermatitis and other dermatoses, said process comprising: administering to the mammal in need thereof a pharmaceutical composition containing an effective amount of an active compound of the formula

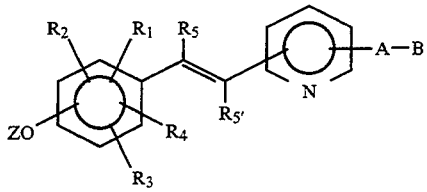

wherein $R_1$, $R_2$, $R_3$ and $R_4$ independently are hydrogen, lower alkyl of 1 to 6 carbons or halogen;

$R_5$ and $R_5'$, independently are hydrogen or lower alkyl of 1 to 6 carbons;

Z is n-alkyl having 1 to 10 carbons, cyclo or branch-chained alkyl of 3 to 10 carbons, and straight chain alkenyl having 2 to 10 carbons;

A is $(CH_2)_n$ where n is 0-5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is $COOR_8$, $CONR_9R_{10}$, $-CH_2OH$, $CH_2OR_{11}$, $CH_2OCOR_{11}$, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2-5 carbons.

2. A process in accordance with claim 1 wherein in the formula of the compound A is $(CH_2)_n$ and n is zero.

3. A process in accordance with claim 1 wherein in the formula of the compound $R_1$ through $R_4$ are hydrogen.

4. A process in accordance with claim 1 wherein in the formula of the compound one of $R_1$ through $R_4$ is lower alkyl and the other is hydrogen.

5. A process in accordance with claim 4 wherein in the formula of the compound the lower alkyl group is in 2-position of the phenyl ring.

6. A process in accordance with claim 1 wherein in the formula of the compound the Z—O— substituent is in the 4 position of the phenyl group.

7. A process in accordance with claim 1 wherein in the formula of the compound the Z—O— substituent is in the 3 position of the phenyl group.

8. A process in accordance with claim 1 wherein in the formula of the compound B is $COOR_8$, or $CONR_9R_{10}$.

9. A process in accordance with claim 1 wherein in the formula of the compound A is $(CH_2)_n$ and n is 0 to 3.

10. A process in accordance with claim 1 wherein the pharmaceutical composition contains approximately 0.001 to 5 percent by weight of the active compound.

11. A process in accordance with claim 10 wherein the pharmaceutical composition is administered systemically.

12. A process in accordance with claim 10 wherein the pharmaceutical composition is administered systemically in a daily dosage of approximately 0.01 to 100 mg/kg body weight of the mammal.

13. A process in accordance with claim 10 wherein the pharmaceutical composition is administered topically.

14. A process in accordance with claim 13 wherein the pharmaceutical composition contains approximately 0.01 to 1 percent by weight of the active compound.

15. A pharmaceutical composition adapted for treating a mammal for the purpose of preventing, curing, alleviating or reversing the diseases or conditions selected from the group consisting of acne, Darier's disease, psoriasis, icthyosis, eczema, atopic dermatitis and other dermatoses, said pharmaceutical composition containing approximately 0.001 to 5 percent by weight of an active compound of the formula

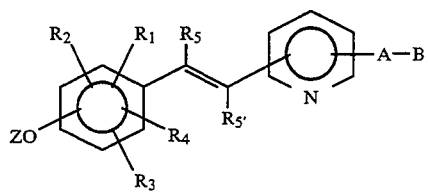

wherein $R_1$, $R_2$, $R_3$ and $R_4$ independently are hydrogen, lower alkyl of 1 to 6 carbons or halogen;

$R_5$ and $R_5'$ independently are hydrogen or lower alkyl of 1 to 6 carbons;

Z is n-alkyl having 1 to 10 carbons, cyclo or branch-chained alkyl of 3 to 10 carbons, and straight chain alkenyl having 2 to 10 carbons;

A is $(CH_2)_n$ where n is 0-5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is $COOR_8$, $CONR_9R_{10}$, $-CH_2OH$, $CH_2OR_{11}$, $CH_2OCOR_{11}$, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2-5 carbons.

* * * * *

UNITED STATES PATENT AND TRADEMARK OFFICE
CERTIFICATE OF CORRECTION

PATENT NO. : 5,434,173
DATED : July 18, 1995
INVENTOR(S) : Chandraratna

It is certified that error appears in the above-indentified patent and that said Letters Patent is hereby corrected as shown below:

Column 3, line 1, "R12" should be --$R_{12}$-- and "R13" should be --$R_{13}$--;

Column 11, line 27, please insert --Reaction Scheme 3--;

Column 13, line 42, "1.,9517" should be --1.9517--;

Column 18, line 22-23, "pheny propen-lyl)" should be

--phenyl)propen-1-yl--;

Column 20, line 16, "methyl2" should be --methyl-2--;

Column 21, line 29, "R10" should be --$R_{10}$--;

Column 21, line 34, "R13" should be --$R_{13}$--;

Column 22, line 53, "R10" should be --$R_{10}$--.

UNITED STATES PATENT AND TRADEMARK OFFICE
CERTIFICATE OF CORRECTION

PATENT NO. : 5,434,173  
DATED : July 18, 1995  
INVENTOR(S) : Chandraratna

Page 2 of 2

It is certified that error appears in the above-indentified patent and that said Letters Patent is hereby corrected as shown below:

Column 8, line 30, "the the" should be --the--;

Column 15, line 46, before "5.83" please insert --(--.

Signed and Sealed this

Twenty-fourth Day of December, 1996

Attest:

BRUCE LEHMAN

Attesting Officer

Commissioner of Patents and Trademarks